United States Patent
Chen et al.

(10) Patent No.: US 11,033,884 B2
(45) Date of Patent: Jun. 15, 2021

(54) CATALYST FOR BENZENE HYDROXYLATION FOR PREPARATION OF PHENOL AND PREPARATION METHOD THEREOF

(71) Applicant: NANJING UNIVERSITY OF TECHNOLOGY, Nanjing (CN)

(72) Inventors: Rizhi Chen, Nanjing (CN); Yaohui Bao, Nanjing (CN); Hong Jiang, Nanjing (CN); Yiqun Fan, Nanjing (CN); Weihong Xing, Nanjing (CN)

(73) Assignee: NANJING UNIVERSITY OF TECHNOLOGY, Jiangsu (CN)

( * ) Notice: Subject to any disclaimer, the term of this patent is extended or adjusted under 35 U.S.C. 154(b) by 0 days.

(21) Appl. No.: 15/028,438

(22) PCT Filed: Sep. 12, 2014

(86) PCT No.: PCT/CN2014/086353
§ 371 (c)(1),
(2) Date: Apr. 11, 2016

(87) PCT Pub. No.: WO2015/051689
PCT Pub. Date: Apr. 16, 2015

(65) Prior Publication Data
US 2016/0250623 A1  Sep. 1, 2016

(30) Foreign Application Priority Data
Oct. 11, 2013 (CN) .......................... 201310474635.0

(51) Int. Cl.
*B01J 29/03* (2006.01)
*C07C 37/58* (2006.01)
*B01J 35/10* (2006.01)
*B01J 37/06* (2006.01)

(52) U.S. Cl.
CPC ....... *B01J 29/0341* (2013.01); *B01J 29/0308* (2013.01); *B01J 29/0316* (2013.01); *B01J 29/0325* (2013.01); *B01J 29/0333* (2013.01); *B01J 35/1061* (2013.01); *B01J 35/1085* (2013.01); *B01J 37/06* (2013.01); *C07C 37/58* (2013.01); *B01J 2229/186* (2013.01); *B01J 2229/32* (2013.01); *Y02P 20/52* (2015.11)

(58) Field of Classification Search
CPC .................. B01J 29/0316; B01J 29/0325; B01J 29/0333; B01J 29/0308; B01J 29/0341; B01J 2229/186; B01J 2229/32; B01J 35/1061; B01J 35/1085; B01J 37/06
USPC .......... 502/60, 200, 240, 244, 247, 262, 253
See application file for complete search history.

(56) References Cited

U.S. PATENT DOCUMENTS

| | | | | |
|---|---|---|---|---|
| 7,767,004 B2 * | 8/2010 | Sayari | ................... | B01D 53/02 264/48 |
| 2008/0276804 A1 * | 11/2008 | Sayari | ................... | B01D 53/02 95/285 |
| 2010/0254890 A1 * | 10/2010 | Yang | ...................... | B01J 20/103 423/592.1 |

FOREIGN PATENT DOCUMENTS

CN   102302946 A   *   1/2012

OTHER PUBLICATIONS

Machine translation of CN 102302946 A, Jan. 2012.*
Yang et al., "Highly Dispersed metal Nanoparticles in Functionalized SBA-15", Chem. Mater., 2003, pp. 275-280.*

* cited by examiner

*Primary Examiner* — Elizabeth D Wood
(74) *Attorney, Agent, or Firm* — PROI Intellectual Property US; Klaus Michael Schmid

(57) ABSTRACT

The invention relates to a catalyst for benzene hydroxylation for preparation of phenol and a preparation method thereof, wherein said catalyst uses a mesoporous material as carrier, and the catalyst is prepared by first modifying the surface of the carrier using aminosilane, then immersing with acetylacetonate salt of metal, and finally washing and drying. Advantage of the invention is that a reactive metal is loaded on the silane-modified mesoporous material to form a homogeneous-heterogeneous composite catalyst, wherein, the reactive metal component is present in a reaction system in a homogeneous form, which ensures high catalytic performance of the catalyst component, and it is loaded on the carrier through bridging action of aminosilane, which improves the acting force between the metal component and the carrier, enhances stability of the catalyst, and facilitates separation of the catalyst from the product. The catalyst has a simple preparation process, has excellent catalytic performance, and can be applied to the reaction system of benzene hydroxylation for preparation of phenol.

2 Claims, 1 Drawing Sheet

CATALYST FOR BENZENE HYDROXYLATION FOR PREPARATION OF PHENOL AND PREPARATION METHOD THEREOF

TECHNICAL FIELD

The invention relates to a preparation method of a homogeneous-heterogeneous composite catalyst, in particular, a catalyst for benzene hydroxylation for preparation of phenol and preparation method thereof, and belongs to the field of catalysis technology.

BACKGROUND

Phenol is an important organic chemical raw material, mainly used for production of phenolic resin, bisphenol A, epoxy resin, caprolactam and aniline, and also has wide applications in synthetic fibers, synthetic rubber, plastic, medicine, pesticides, flavors, dyes, paints and the like. Now in the world, the industrial production of phenol is mainly realized through the cumene method. This process has high energy consumption and low phenol yield, and produces a large amount of acetone as co-product; furthermore, a plurality of organic reagents are added into the reaction, which causes resource wasting, inconvenient operation and serious environmental pollution. In recent years, synthesis of phenol in one step by direct benzene hydroxylation has become a hot research topic. This method has simple process, little environmental pollution and other characteristics, is an environmental-friendly catalytic process, and has very wide prospects of industrial development and applications.

Oxidant used for direct catalytic oxidation of benzene for preparation of phenol generally comprises oxygen, $N_2O$ and $H_2O_2$. Oxygen is abundant and low cost. Therefore, preparation of phenol by direct oxidation of benzene with oxygen as oxidant is the way with the most development value and application prospect. At present, the method for preparation of phenol by oxidation of benzene with oxygen mainly includes a gas phase method and a liquid phase method. The gas phase method is a high-temperature reaction, and problems such as catalyst deactivation and deep product oxidization easily occur during the reaction process. The liquid phase method has a relatively low reaction temperature, and a mild reaction condition, which attracts broad attention. The key of the liquid phase method is to design a catalyst for activating oxygen molecules. The reactive component of the catalyst is generally a metal, for example copper, vanadium, palladium, and iron. In the reaction process, loss of the metal component of the catalyst is the bottleneck problem to restrict the application of such catalyst. Therefore, development of high-performance catalysts is the focus of research for preparation of phenol by benzene hydroxylation.

At present, the catalysts disclosed in the existing patents are mainly supported catalysts; the carriers used are mainly $SiO_2$, C or $Al_2O_3$; the reactive components are mainly palladium, platinum, copper, vanadium, iron or zinc. Chinese patent applications CN1102452901A and CN102463124A mention the preparation of supported catalysts, and their usage for preparation of phenol by benzene hydroxylation. Preparation of these catalysts generally requires calcination and has high preparation cost. Furthermore, in the reaction process, the metal component is dissolved and then lost into the reaction solution, which leads to loss and activity decrease of the catalyst, and which also affects purity of products.

SUMMARY OF THE INVENTION

An objective of the invention is to overcome the problem of easy loss and poor stability of the existing catalyst for benzene hydroxylation for preparation of phenol in the reaction system, and provide a catalyst for benzene hydroxylation for preparation of phenol. Another objective of the invention is to provide a preparation method of above catalyst, link the reactive component of the catalyst to carrier through aminosilane to form a homogeneous-heterogeneous composite catalyst, enhance the acting force between the reactive component and the carrier, and improve catalytic performance of the catalyst.

Technical scheme of the invention is as follows: a mesoporous material is used as a carrier; its channel surface is functionalized using aminosilane, then a reactive metal component is loaded onto the aminosilane-modified mesoporous material through an immersion method to prepare a homogeneous-heterogeneous composite catalyst with high performance. Aminosilane (such as γ-aminopropyltriethoxysilane KH550) has two functional groups: one functional group alkoxy can be condensed with hydroxyl on the surface of the mesoporous carrier to form a chemical bond such as Si—O—Si or Al—O—Si; the other functional group —$NH_2$ has a pair of lone pair electrons, can form a coordination bond with metal ions, and firmly adsorb the reactive metal component. As a result, functionally modifying the carrier surface with aminosilane such as KH550 and then loading the reactive metal component onto the modified carrier can realize compounding of the homogeneous catalytic reactive component and the heterogeneous carrier, wherein, the reactive metal component is present in the reaction system in a homogeneous form, which ensures high catalytic performance of the catalyst component; meanwhile, the reactive metal component is loaded on the carrier through bridging action of aminosilane, which facilitates separation of the catalyst from the product, and ensures that the catalyst still keeps good catalytic performance after repeated use.

The specific technical scheme of the invention is: a catalyst for benzene hydroxylation for preparation of phenol, wherein: a mesoporous material SBA-15, SBA-16 or MCM-41 with its channel surface functionally modified using aminosilane is used as a carrier; palladium, platinum, copper, vanadium, iron or zinc is used as a reactive component; a homogeneous-heterogeneous composite catalyst is prepared by loading the reactive component onto the aminosilane-modified mesoporous material through an immersion method. The reactive metal component is loaded onto the carrier through bridging action of the aminosilane, which improves the acting force between the metal component and the carrier, enhances stability of the catalyst, and facilitates separation of the catalyst from the product; furthermore, the reactive metal component is present in a reaction system in a homogeneous form, which ensures high catalytic performance of the catalyst component. Preferably the reactive component is copper or vanadium.

The invention also provides a method for preparing the above catalyst, and the specific steps are:

A. carrier surface modification process: immersing a carrier into an aminosilane solution with a concentration of 0.1-2 g/L, performing surface modification at a temperature of 20-40° C., taking out, washing and air drying;

B. immersion process: immersing the modified carrier obtained from the step A into acetylacetonate solution containing reactive components being palladium, platinum, copper, vanadium, iron or zinc, at a temperature of 20-40° C. for 6-36 h, wherein the immersion solution has a concentration of 0.1-0.25 mol/L; and C. washing and drying process: washing the catalyst obtained from the step B with absolute ethanol or dichloromethane and drying.

Preferably in the step A the aminosilane is γ-aminopropyltriethoxysilane (KH550), N-(β-aminoethyl)-γ-aminopropyltrimethoxysilane (KH792) or N-(β-aminoethyl)-γ-aminopropylmethyldimethoxysilane (silane coupling agent 602); the solvent is dichloromethane, toluene or absolute ethanol; and the modification time is 1-32 h.

The invention employs the following conditions to perform activity evaluation of the catalyst.

Reaction is performed in 150 ml three-neck flask. 40 ml of glacial acetic acid, 10 ml of distilled water, 2 g of benzene, 4 g of ascorbic acid and 0.5 g of catalyst are added into the reaction flask sequentially, the inlet oxygen flow is adjusted to 30 ml/min, the temperature is maintained constant at 30° C., a sample is collected after 6 h of reaction, the product is analyzed by high performance liquid chromatography, and benzene conversion and phenol selectivity are calculated according to a standard curve.

Beneficial Effects

In the invention the reactive component is loaded onto the aminosilane-modified mesoporous material through an immersion method to form a homogeneous-heterogeneous composite catalyst, wherein, the reactive metal component is present in the reaction system in a homogeneous form, which ensures high catalytic performance of the catalyst component; meanwhile, the reactive metal component is loaded on the carrier through bridging action of aminosilane, which facilitates separation of the catalyst from the product, and ensures that the catalyst still keeps good catalytic performance after repeated use.

DETAILED DESCRIPTION OF THE PREFERRED EMBODIMENTS

Effects of the catalyst and the preparation method of the invention are further illustrated below through Examples.

Example 1 Preparation of V/NH$_2$-SBA-15 Catalyst 2 g of SBA-15 is dispersed in 50 ml of dichloromethane solvent, and 0.05 g of aminosilane KH550 is added, stirred at 25° C., immersed for 1 h, washed with absolute ethanol, filtered and then dried to obtain NH$_2$-SBA-15 powder. 1.33 g of VO(C$_5$H$_7$O$_2$)$_2$ (molecular weight of 265.15) is added to 50 ml of CH$_2$Cl$_2$, and stirred. After the solid is completely dissolved, 1.5 g of the NH$_2$-SBA-15 powder is added, stirred at 40° C., filtered after 12 h of immersion, washed with absolute ethanol, and dried at 90° C. to obtain V/NH$_2$-SBA-15 catalyst.

Figure 1:
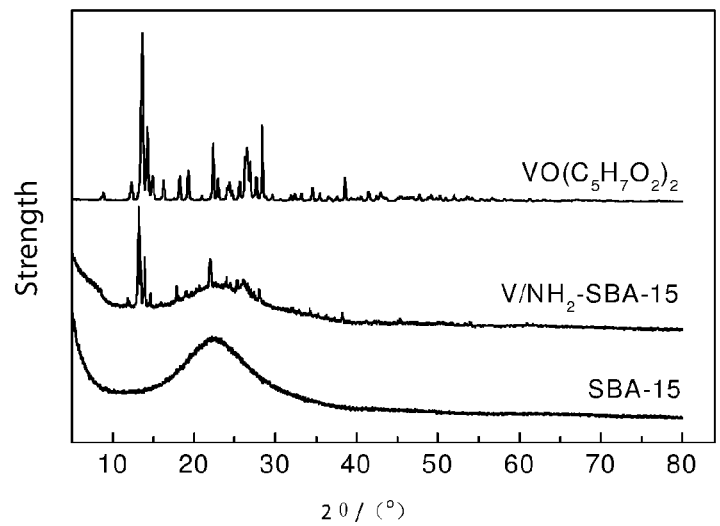
FIG. 1 is X-ray diffraction diagrams of SBA-15 carrier, V/NH$_2$-SBA-15 (Example 1) catalyst and vanadiumoxy acetylacetonate (VO(C$_5$H$_7$O$_2$)$_2$) precursor.

FIG. 1 shows the analysis result of X-ray diffraction of the V/NH$_2$-SBA-15 catalyst. SBA-15 has a strong peak at 22°, corresponding to amorphous Si. V/NH$_2$-SBA-15 presents characteristic peaks of VO(C$_5$H$_7$O$_2$)$_2$ and Si, which indicates that the catalyst component has been loaded on the SBA-15 carrier.

Figure 2:
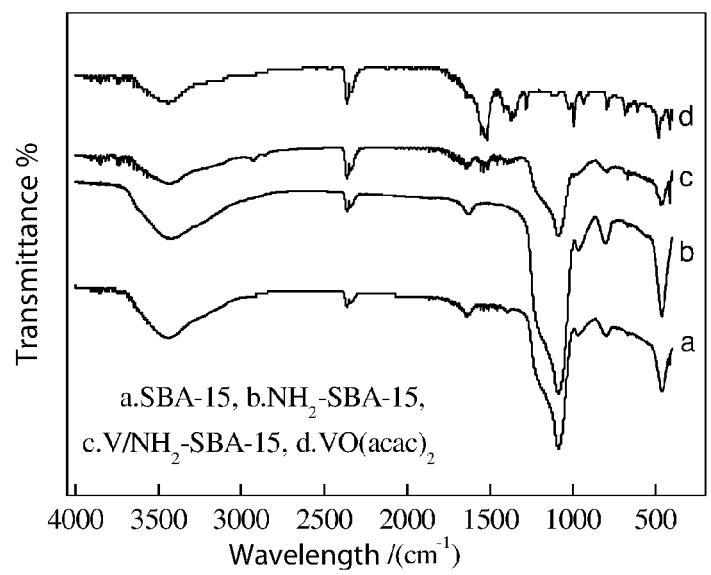
FIG. 2 is infrared characterization diagrams of SBA-15, NH$_2$-SBA-15 (Example 1), VO(C$_5$H$_7$O$_2$)$_2$ and V/NH$_2$-SBA-15.

From FIG. 2, the peak at 960 cm$^{-1}$ corresponds to Si—OH. The strength of V/NH$_2$-SBA-15 significantly decreases at 960 cm$^{-1}$, which is due to silane functionalization of the carrier and loading of VO(C$_5$H$_7$O$_2$)$_2$. Furthermore, it can be found by comparing c and a that c has additional two peaks at 2930 and 2848 cm$^{-1}$, which correspond to C—H stretching vibration, while 1557 cm$^{-1}$ corresponds to bending vibration, which indicates that silane is grafted onto the surface of SBA-15 through a chemical bond.

The catalyst is used in a system for preparation of phenol by benzene hydroxylation. After 6 h of reaction, the yield of phenol is 4.5%. After the catalyst is used for 5 times, the catalytic efficiency is reduced to 70% of that of fresh catalyst.

Example 2 Preparation of V/NH$_2$-MCM-41 Catalyst 2 g of MCM-41 is dispersed in 50 ml of dichloromethane solvent, and 0.1 g of aminosilane KH792 is added, stirred at 20° C., immersed for 8 h, washed with absolute ethanol, filtered and then dried to obtain NH$_2$-MCM-41 powder. 3.31 g of VO(C$_5$H$_7$O$_2$)$_2$ (molecular weight of 265.15) is added to 50 ml of CH$_2$Cl$_2$, and stirred. After the solid is completely dissolved, 1.5 g of the NH$_2$-MCM-41 powder is added, stirred at 20° C., filtered after 6 h immersion, washed with absolute ethanol, and dried at 90° C. to obtain V/NH$_2$-MCM-41 catalyst.

The catalyst is used in a system for preparation of phenol by benzene hydroxylation, and after 6 h of reaction, the yield of phenol is 3.9%. After the catalyst is used for 5 times, the catalytic efficiency is reduced to 62% of that of fresh catalyst.

Example 3 Preparation of Pd/NH$_2$-SBA-15 Catalyst 2 g of SBA-15 is dispersed in 50 ml of dichloromethane solvent, and 0.05 g of aminosilane KH550 is added, stirred at 40° C., immersed for 24 h, washed with absolute ethanol, filtered and then dried to obtain NH$_2$-SBA-15 powder. 3.05 g of Pd(C$_5$H$_7$O$_2$)$_2$ (molecular weight of 304.64) is added to 50 ml of CH$_2$Cl$_2$, and stirred. After the solid is completely dissolved, 1.5 g of the NH$_2$-SBA-15 powder is added, stirred at 40° C., filtered after 36 h of immersion, washed with absolute ethanol, and dried at 90° C. to obtain Pd/NH$_2$-SBA-15 catalyst.

The catalyst is used in a system for preparation of phenol by benzene hydroxylation, and after 6 h of reaction, the yield of phenol is 2.5%. After the catalyst is used for 5 times, the catalytic efficiency is reduced to 60% of that of fresh catalyst.

Example 4 Preparation of Cu/NH$_2$-SBA-16 Catalyst 2 g of SBA-16 is dispersed in 50 ml of dichloromethane solvent, and 0.005 g of silane coupling agent 602 is added, stirred at 30° C., immersed for 32 h, washed with absolute ethanol, filtered and then dried to obtain NH$_2$-SBA-16 powder. 1.96 g of Cu(C$_5$H$_7$O$_2$)$_2$ (molecular weight of 261.76) is added to 50 ml of CH$_2$Cl$_2$, and stirred. After the solid is completely dissolved, 1.5 g of the $NH_2$-SBA-16 powder is added, stirred at 25° C., filtered after 12 h of immersion, washed with absolute ethanol, and dried at 90° C. to obtain Cu/$NH_2$-SBA-16 catalyst.

The catalyst is used in a system for preparation of phenol by benzene hydroxylation, and after 6 h of reaction, the yield of phenol is 3.1%. After the catalyst is used for 5 times, the catalytic efficiency is reduced to 65% of that of fresh catalyst.

What is claimed is:

1. A method for preparing a catalyst for benzene hydroxylation for preparation of phenol, wherein the catalyst comprises a carrier being a mesoporous material SBA-16, SBA-16 or MC M-41 with its channel surface functionally modified using aminosilane, and a reactive component being palladium, platinum, copper, vanadium, iron or zinc; wherein the catalyst is a homogeneous-heterogeneous composite catalyst; and wherein the reactive component is loaded onto the carrier through bridging action of the aminosilane, the method comprising the following steps:
   A. carrier surface modification process: immersing the carrier into an aminosilane solution with a concentration of 0.1-2 g/L, performing surface modification at a temperature of 20-40° C. taking out, washing and air drying;
   B. immersion process: immersing the modified carrier obtained from the step A into acetylacetonate solution containing the reactive component at a temperature of 20-40° C. for 6-36 hours; wherein the acetylacetonate solution has a concentration of 0.1-0.25 mol/L; and
   C. washing and drying process: washing the catalyst obtained from the step B with absolute ethanol or dichloromethane and drying
   wherein the temperature used in both the method steps A and B does not exceed 40° C.

2. The preparation method according to claim 1, wherein in the step A the aminosilane is γ-aminopropyltriethoxysilane, N-(β-aminoethyl)-γ-aminopropyltrimethoxysilane, or N-(β-aminoethyl)-γ-aminopropylmethyldimethoxysilane;
   the solvent is dichloromethane, toluene or absolute ethanol; and
   the modification time is 1-32 hours.

* * * * *